(12) United States Patent
Dorian

(10) Patent No.: US 10,406,534 B2
(45) Date of Patent: Sep. 10, 2019

(54) BLOOD WASHING AND SEPARATION SYSTEM

(71) Applicant: Randel E. Dorian, San Diego, CA (US)

(72) Inventor: Randel E. Dorian, San Diego, CA (US)

(73) Assignee: Hanuman Medical, San Francisco, CA (US)

( * ) Notice: Subject to any disclaimer, the term of this patent is extended or adjusted under 35 U.S.C. 154(b) by 87 days.

(21) Appl. No.: 15/828,481

(22) Filed: Dec. 1, 2017

(65) Prior Publication Data

US 2018/0154373 A1   Jun. 7, 2018

Related U.S. Application Data

(60) Provisional application No. 62/429,299, filed on Dec. 2, 2016.

(51) Int. Cl.
| | |
|---|---|
| *B04B 5/04* | (2006.01) |
| *B04B 1/04* | (2006.01) |
| *B04B 1/12* | (2006.01) |
| *A61M 1/36* | (2006.01) |

(52) U.S. Cl.
CPC .............. *B04B 5/04* (2013.01); *A61M 1/3693* (2013.01); *B04B 1/04* (2013.01); *B04B 1/12* (2013.01); *B04B 5/0428* (2013.01); *B04B 5/0442* (2013.01); *A61M 2202/0429* (2013.01); *B04B 2005/045* (2013.01)

(58) Field of Classification Search
CPC ........ A61M 1/3693; A61M 2202/0429; B04B 1/04; B04B 1/12; B04B 5/04; B04B 5/0428; B04B 5/0442; B04B 2005/045
See application file for complete search history.

(56) References Cited

U.S. PATENT DOCUMENTS

| | | | | |
|---|---|---|---|---|
| 3,080,108 | A * | 3/1963 | Jacobson | .................. B04B 1/12 494/30 |
| 4,854,933 | A * | 8/1989 | Mull | ..................... B04B 5/0407 494/38 |
| 8,540,078 | B2 * | 9/2013 | Leach | ................ B01D 17/0217 210/360.1 |
| 2008/0011684 | A1 * | 1/2008 | Dorian | ................ A61M 1/3496 210/669 |
| 2018/0154286 | A1 | 6/2018 | Dorian | |
| 2018/0154374 | A1 | 6/2018 | Dorian | |

* cited by examiner

*Primary Examiner* — Timothy C Cleveland
(74) *Attorney, Agent, or Firm* — Schwegman Lundberg & Woessner, P.A.

(57) ABSTRACT

A separation rotor having an outer wall defining a separation chamber and an inner annular wall dividing the separation chamber into an inner annular space and an outer annular space. The separation rotor can be rotated to move heavier and/or denser components of the multi-component fluid into the outer annular space. The lighter and/or less dense components of the multi-component fluid can be retained within the inner annular space. The inner annular space and the outer annular space separation rotor can be selectively accessed to withdraw the components retained within the inner annular space and the outer annular spaces.

20 Claims, 19 Drawing Sheets

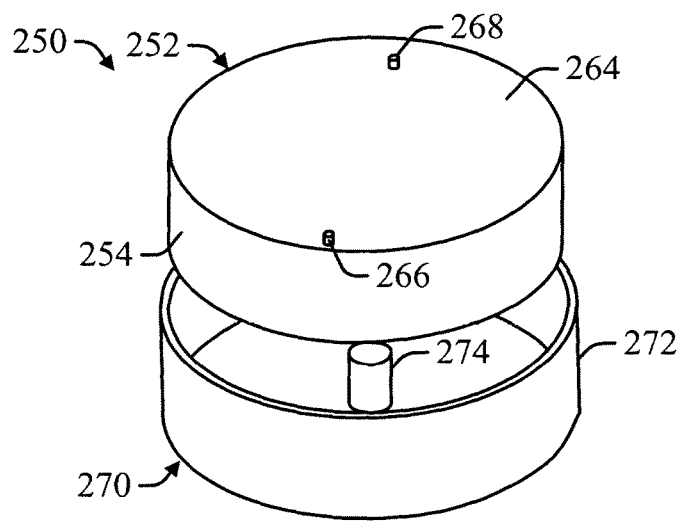
FIG. 20
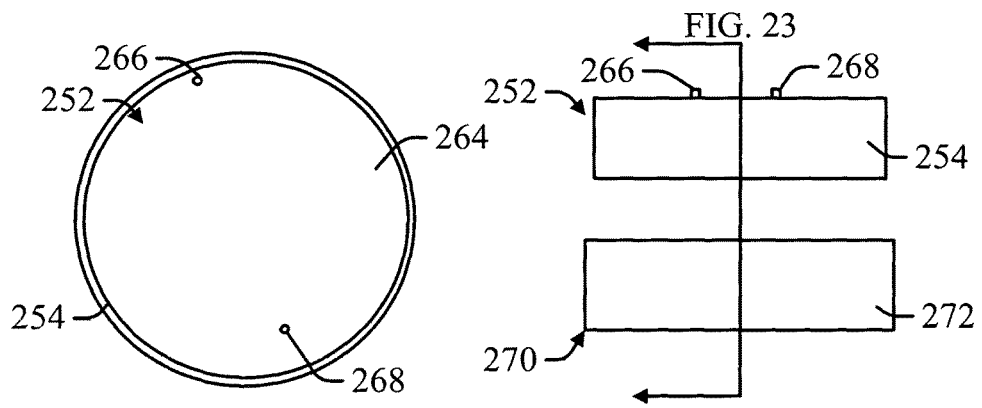
FIG. 21  FIG. 22

BLOOD WASHING AND SEPARATION SYSTEM

CLAIM OF PRIORITY

This patent application claims the benefit of priority, under 35 U.S.C. Section 119(e), to Randel E. Dorian, U.S. Patent Application Ser. No. 62/429,299, entitled "BLOOD WASHING AND SEPARATION SYSTEM," filed on Dec. 2, 2016, each of which is hereby incorporated by reference herein in its entirety.

TECHNICAL FIELD

This document pertains generally, but not by way of limitation, to separation systems and related methods for separating of components of a multiple component material.

BACKGROUND

Whole blood can often be fractionated to separate red blood cells, platelets, and other cellular material from whole blood fluids such that the cellular material can be isolated and extracted. The collected cellular material can be further processed by adding one or more wash fluids to the collected cellular material to remove any remaining plasma on the cellular material and undesirable fluids or materials. The wash solution containing the collected cellular material can be centrifuged to separate the collected cellular material from the wash fluids. The washed cellular material can be difficult to extract from the separated wash fluids and collected in a separate storage container or apparatus without contamination of the cellular material.

OVERVIEW

The present inventors have recognized, among other things, that a problem to be solved can include separating components of a multi-component fluid and selectively extracting the separated components. In an example, the present subject matter can provide a solution to this problem, such as by providing a separation rotor having an outer wall defining a separation chamber and an inner annular wall dividing the separation chamber into an inner annular space and an outer annular space. The outer annular space can be arranged concentrically around the inner annular space. The separation rotor can be rotated to move heavier and/or denser components of the multi-component fluid into the outer annular space. The lighter and/or less dense components of the multi-component fluid can be retained within the inner annular space. The inner annular space and the outer annular space of the separation chamber can be selectively accessed to withdraw the components retained within the inner annular space and the outer annular spaces.

This overview is intended to provide an overview of subject matter of the present patent application. It is not intended to provide an exclusive or exhaustive explanation of the present subject matter. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 20 is a perspective exploded view of a drum rotor and a rotor cup according to an example of the present disclosure.

FIG. 21 is a top exploded view of a drum rotor and a rotor cup according to an example of the present disclosure.

FIG. 22 is a side exploded view of a drum rotor and a rotor cup according to an example of the present disclosure.

DETAILED DESCRIPTION

Figure 1:
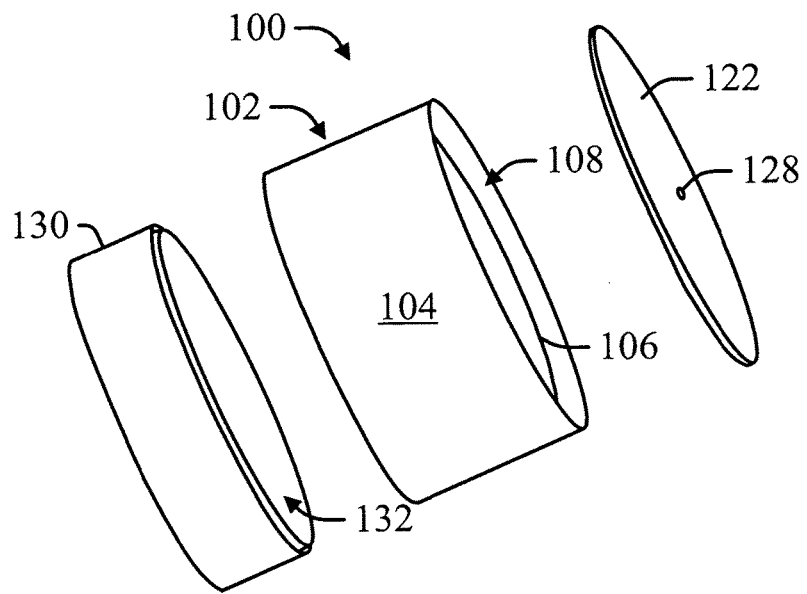
FIG. 1 is a perspective exploded view of a drum rotor according to an example of the present disclosure.
Figure 2:
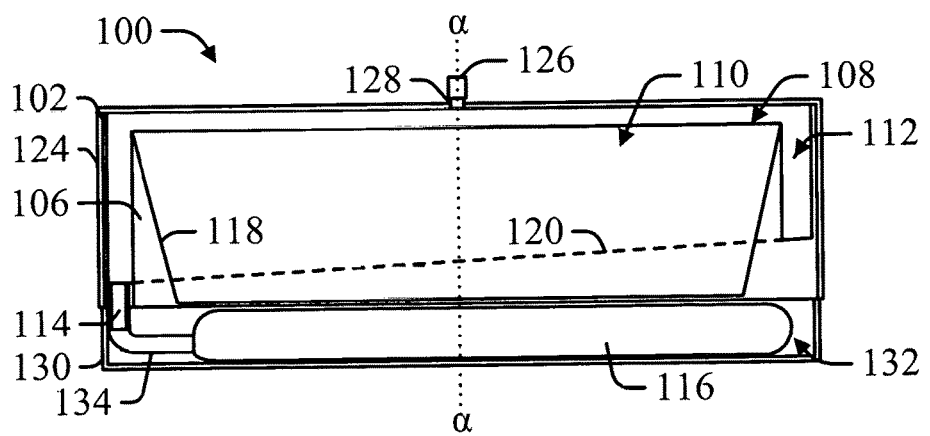
FIG. 2 is a cross-sectional side view of a drum rotor according to an example of the present disclosure.

As depicted in FIGS. 1-2 and 5-6, in an example, a drum rotor 100 for separating components of a multi-component fluid can include a separation rotor 102 including an outer wall 104 and an inner annular wall 106. The outer wall 104 can define a separation chamber 108 within the separation rotor 102 for receiving the multi-component fluid. As illustrated in FIG. 2, the inner annular wall 106 can be positioned to divide the separation chamber 108 into an inner annular space 110 and an outer annular space 112 arranged concentrically around the inner annular space 110. The separation rotor 102 can further include an outlet drain 114 defining an opening in the outer wall 104 at the outer annular space 112 to permit drainage of material from the outer annular space 112. As depicted in FIGS. 2 and 4B, in an example, a fluid bag 116 can be fluidly connected to the outlet drain 114 to receive material draining through the outlet drain 114.

In an example, a multi-component fluid can be placed within the inner annular space 110. The multi-component fluid can comprise, but is not limited to, a wash solution in which wash fluids are added to cellular material to cleanse the cellular material. The drum rotor 100 can be rotated about a rotational axis α-α transecting the center of the separation rotor 102 such that denser materials or fluids (e.g. cellular material) are forced radially outward from the rotational axis α-α and over the inner annular wall 106 into the outer annular space 112. As depicted in FIG. 2, in an example, the inner annular wall 106 can include an angled ramp face 118 slanted toward the rotational axis to facilitate movement of the separated material over the inner annular wall 106. Light materials or fluids (e.g. wash fluids) remain proximate the rotational axis α-α and are generally retained within the inner annular space 110. In certain examples, a portion of the lighter materials or fluids can enter the outer annular space 112. During rotation of the drum rotor 100, a brake can be applied to the drum rotor 100 quickly stop the rotation of the drum rotor 100 to re-suspend separated solids captured in the outer annular space 112 within fluids in the outer annular space 112.

The material collected in the outer annular space 112 can drain through the outlet drain 114 into the connected fluid bag 116. As depicted in FIG. 2, in an example, the separation rotor 102 can include an angled floor 120 slanted toward the outlet drain 114 to direct material collected in the outer annular space 112 toward the outlet drain 114. In certain examples, the collected material can drain through the outlet drain 114 during rotation of the drum rotor 100 or after immediately following braking of the rotation of the drum rotor 100 as the material within the outer annular space 112 settles. In this configuration, the fluid bag 116 can remain connected to the separation rotor 102 during rotation of the separation rotor 102. Following the separation and collection of the separated materials within the fluid bag 116, the fluid bag 116 can be disconnected from the separation rotor 102. In an example, the drum rotor 100 can be a single use disposable.

Figure 3:
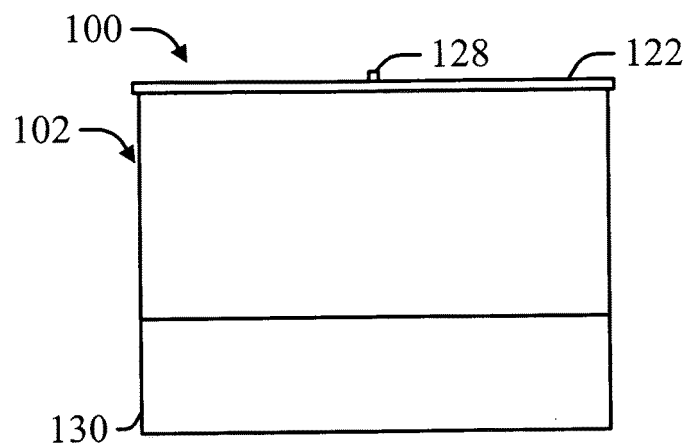
FIG. 3 is a side view of a drum rotor according to an example of the present disclosure.
Figure 4A:
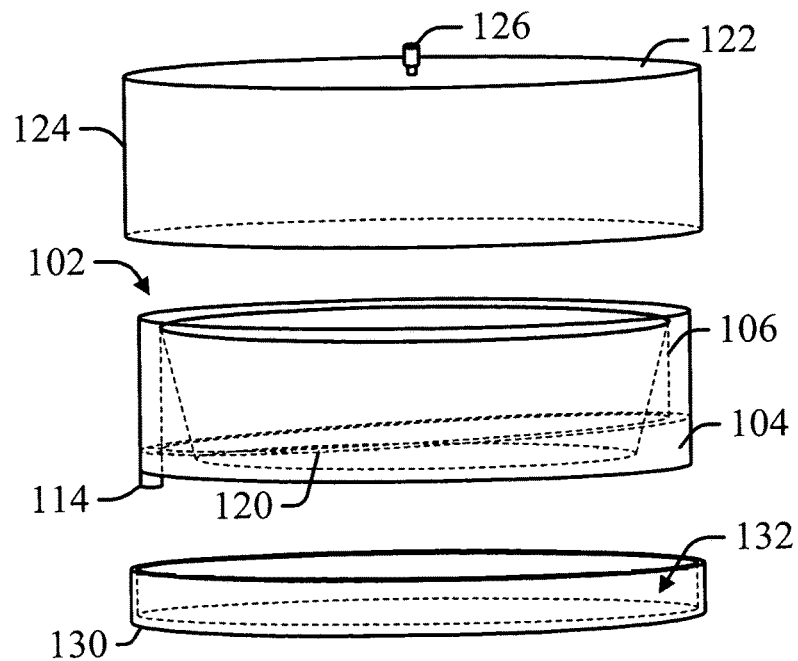
FIG. 4A is a perspective exploded, partial cross-sectional view of a drum rotor according to an example of the present disclosure.
Figure 4B:
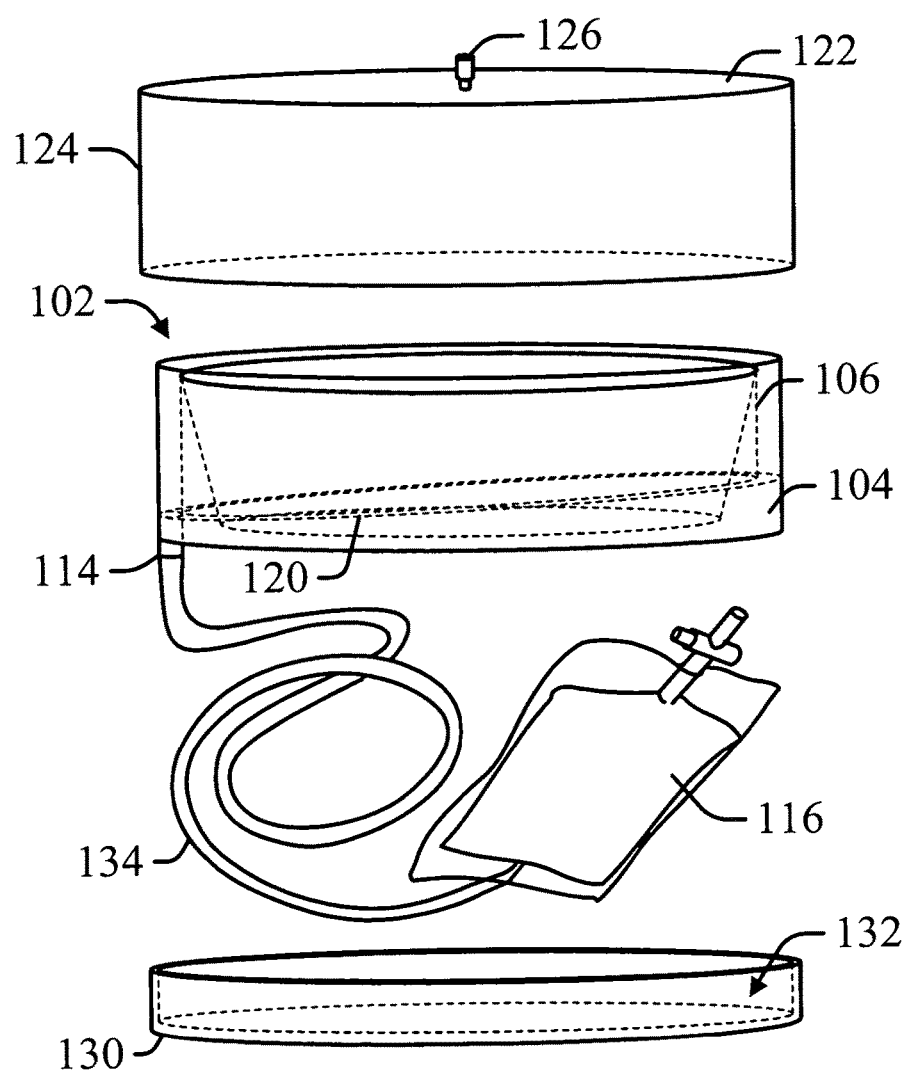
FIG. 4B is a perspective exploded, partial cross-sectional view of a drum rotor with an attached fluid bag according to an example of the present disclosure.
Figure 5:
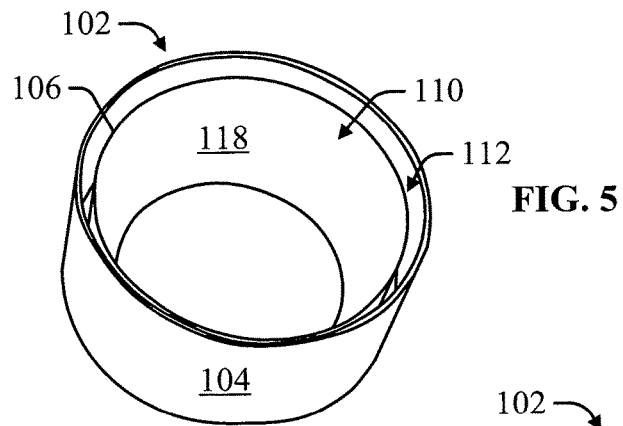
FIG. 5 is a top perspective view of a separation rotor of a drum rotor according to an example of the present disclosure.
Figure 6:
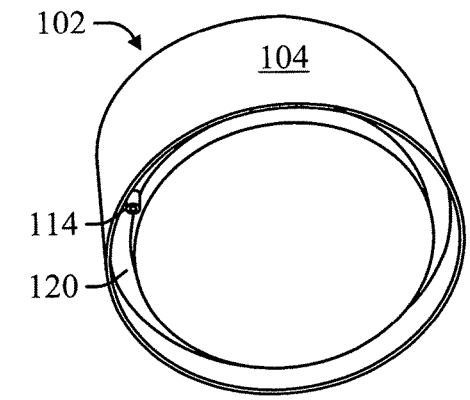
FIG. 6 is a bottom perspective view of a separation rotor of a drum rotor according to an example of the present disclosure.

As depicted in FIGS. 1-4, in an example, the drum rotor 100 can include a top cap 122 that can be coupled to the separation rotor 102 to enclose the separation chamber 106. The top cap 122 can be planar as illustrated in FIGS. 1 and 3 or can comprise sidewalls 124 that can enclose at least a portion of the separation rotor 102 as illustrated in FIGS. 2 and 4. The inner annular wall 106 can be shorter than the outer wall 104 such that a gap is defined between the top cap 122 and inner annular wall 106 when the top cap 122 is coupled to the separation rotor 102. In this configuration, the separated material passes from the inner annular space 110 through the gap into the outer annular space 112.

In an example, the top cap 122 can include an inlet port 126 defining an inlet opening 128. The top cap 122 can also include only an inlet opening 128 as illustrated in FIG. 1. In operation, a container containing the multi-component material can be fluidly coupled to the inlet port 126 for feeding the multi-component material through the inlet opening 128 into the separation chamber 108. The inlet opening 128 can be positioned on the top cap 122 such that the multi-component material entering through the inlet opening 128 enters the inner annular space 110.

Figure 7:
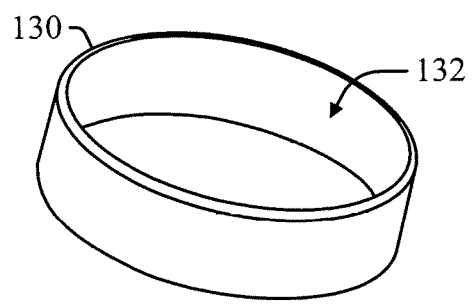
FIG. 7 is a perspective view of a bottom cap of a separation rotor according to an example of the present disclosure.

As depicted in FIGS. 2, 4B and 7, the drum rotor 100 can include a bottom cap 130 defining a bag chamber 132 for receiving the fluid bag 116. The bottom cap 130 can be coupled to at least one of the separation rotor 102 and the side walls 124 of the top cap 122 to enclose the fluid bag 116 coupled to the outlet drain 114. The bottom cap 130 can permit the fluid bag 116 to rotate with the separation rotor 102 during separation of the multi-component material to permit collection of the separated material during rotation or as the separated material settles following braking of the separation rotor 102.

In an example, the fluid bag 116 can be pre-sterilized such that the separated material remains sterile following the separation of the multi-component and during collection within the fluid bag 116. The drum rotor 100 can also be a pre-sterilized, single-use disposable. The connector tube 134 can also be sterile to prevent contamination of the separated material passing through the fluid bag 116.

Figure 8:
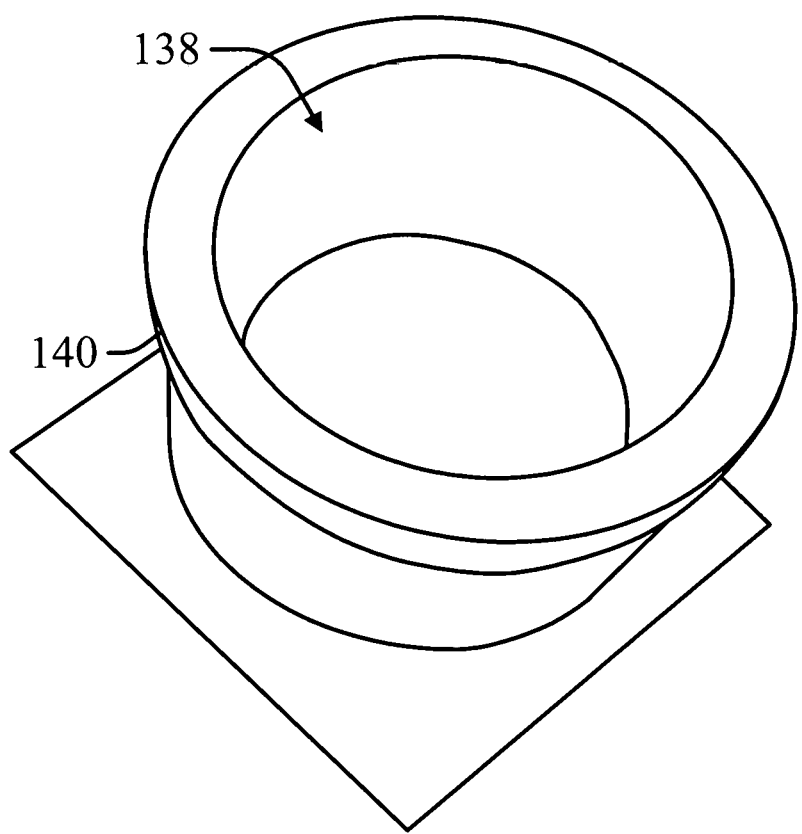
FIG. 8 is a perspective view of a centrifuge cup for receiving a drum rotor according to an example of the present disclosure.

As depicted in FIG. 8, the drum rotor 100 can be received within an interior space 138 of a centrifuge cup 140 rotatable about the rotational axis α-α. In this configuration, the centrifuge cup 140 can be sized to engage at least one of the separation rotor 102, the top cap 122, and the bottom cap 130 such that rotation of the centrifuge cup 140 rotates the drum rotor 100.

Figure 9:
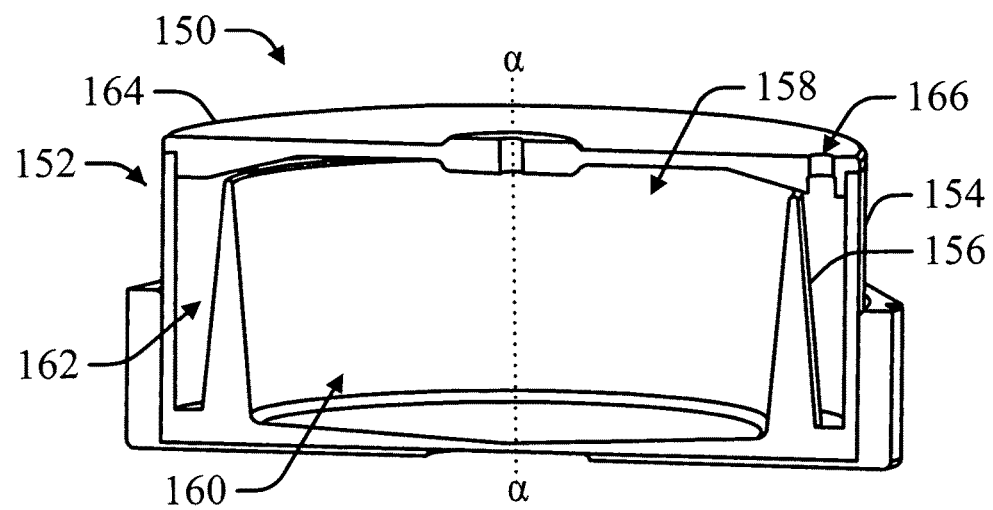
FIG. 9 is a cross-sectional perspective view of a drum rotor received in a rotor cup according to an example of the present disclosure.
Figure 10:
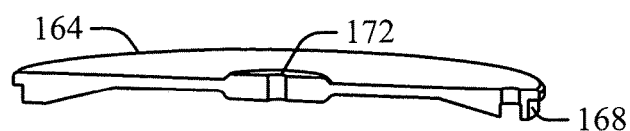
FIG. 10 is a cross-sectional perspective view of a top cap according to an example of the present disclosure.
Figure 11:
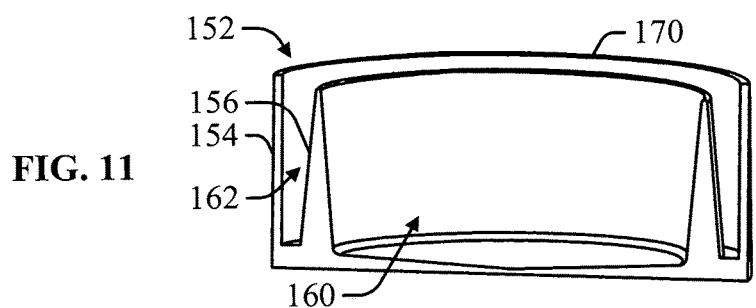
FIG. 11 is a cross-sectional perspective view of a separation rotor according to an example of the present disclosure.
Figure 12:
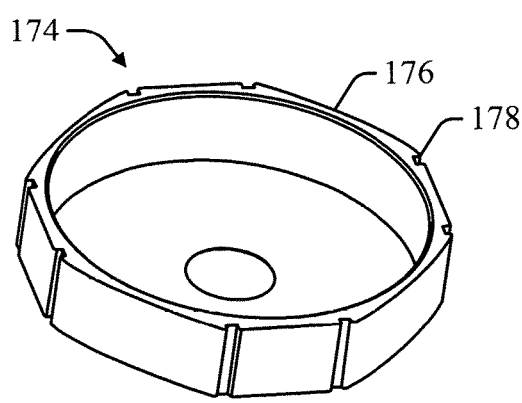
FIG. 12 is a perspective view of a rotor cup according to an example of the present disclosure.

As depicted in FIGS. 9-12, in an example, a drum rotor 150 for separating components of a multi-component fluid can include a separation rotor 152 including an outer wall 154 and an annular inner wall 156. The outer wall 154 can define a separation chamber 158 within the separation rotor 102 for receiving the multi-component fluid. As illustrated in FIG. 9, the inner annular wall 156 can be positioned to divide the separation chamber 158 into an inner annular space 160 and an outer annular space 162 arranged concentrically around the inner annular space 160. The drum rotor 150 can include a top cap 164 that can be coupled to the separation rotor 152 to enclose the separation chamber 156. The top cap 164 can include a withdrawal port 166 aligned with the outer annular space 162.

In an example, a multi-component fluid can be placed within the inner annular space 160. The multi-component fluid can comprise, but is not limited to, a wash solution in which wash fluids are added to cellular material to cleanse the cellular material. The drum rotor 150 can be rotated about a rotational axis α-α transecting the center of the separation rotor 152 such that denser materials or fluids (e.g. cellular material) are forced radially outward from the rotational axis α-α and over the inner annular wall 156 into the outer annular space 162. Light materials or fluids (e.g. wash fluids) remain proximate the rotational axis α-α and are generally retained within the inner annular space 160. In certain examples, a portion of the lighter materials or fluids can enter the outer annular space 162. During rotation of the drum rotor 150, a brake can be applied to the drum rotor 150 to quickly stop the rotation of the drum rotor 150 to re-suspend separated solids captured in the outer annular space 162 within fluids in the outer annular space 162. A withdrawal member for a collection container can be inserted through the withdrawal port 166 into the outer annular space 162 to withdraw material collected within the outer annular space 162.

In an example, the top cap 164 can include an engagement portion 168 that can engage a top edge 170 of the separation rotor 152 to enclose the separation chamber 158. The inner annular wall 156 can be shorter than the outer wall 154 such that a gap is defined between the top cap 164 and inner annular wall 156 when the top cap 164 is coupled to the separation rotor 158. In this configuration, the separated material passes from the inner annular space 160 through the gap into the outer annular space 162.

In an example, the top cap 164 can include an inlet port 166 defining an inlet opening 168. In operation, a container containing the multi-component material can be fluidly coupled to the inlet port 166 for feeding the multi-component material through the inlet opening 168 into the separation chamber 158. The inlet opening 168 can be positioned on the top cap 162 such that the multi-component material entering through the inlet opening 168 enters the inner annular space 160.

Figure 13:
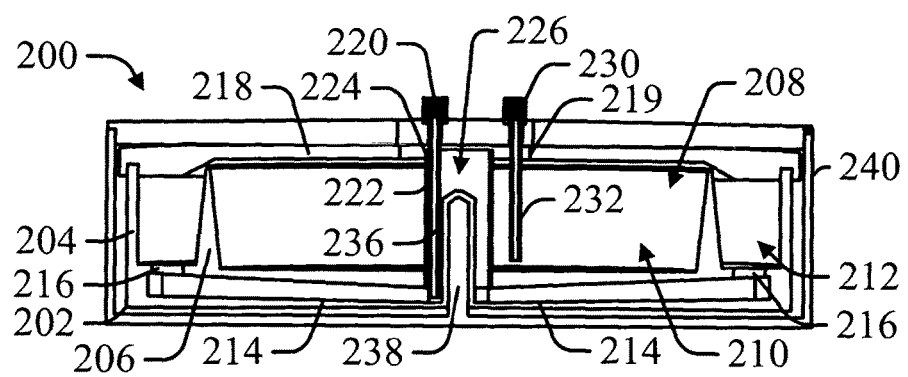
FIG. 13 is a cross-sectional side view of a drum rotor according to an example of the present disclosure.

As depicted in FIGS. 9 and 13, the separation rotor 152 can be received within a rotor cup 174. The rotor cup 174 can include a sidewall 176 defining a rotor space for receiving the separation rotor 152. In an example, the sidewall 176 of the rotor cup 174 can comprise at least one engagement feature 178 for engaging the rotor cup 174 to a centrifuge for rotation of the separation rotor 152 about the rotational axis α-α.

Figure 14:
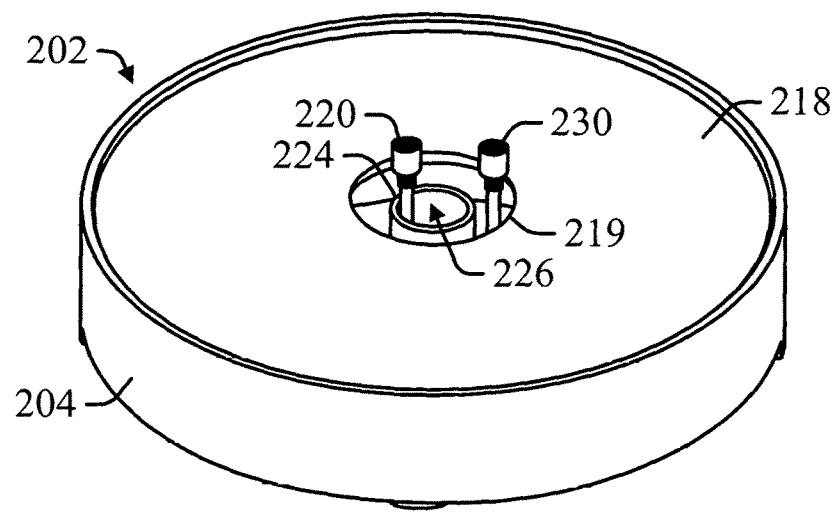
FIG. 14 is a perspective view of a drum rotor according to an example of the present disclosure.
Figure 15:
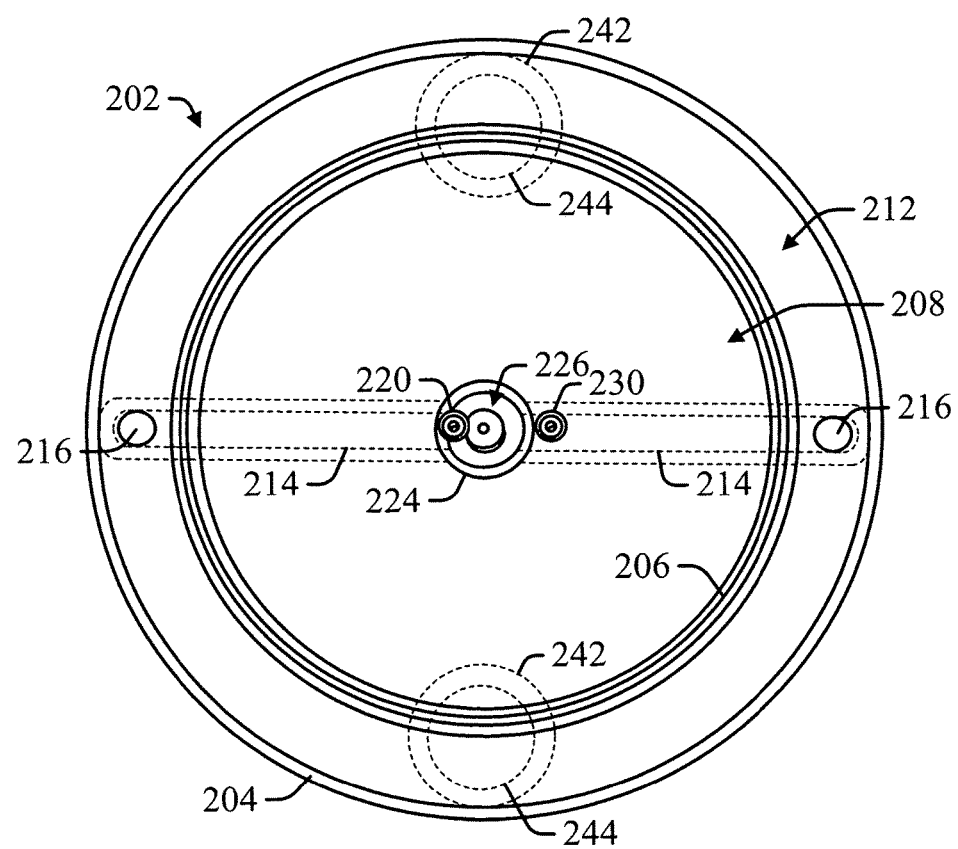
FIG. 15 is a top cross-sectional view of a drum rotor according to an example of the present disclosure.
Figure 16:
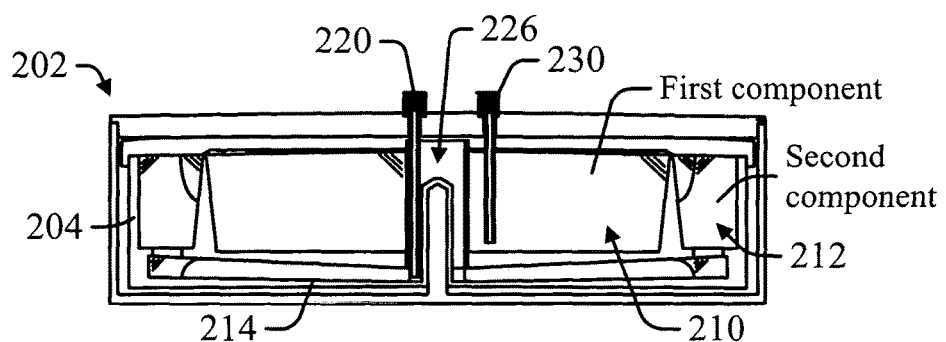
FIG. 16 is a cross-sectional side view of a drum rotor during centrifugation to fractionate a cell wash solution containing cellular fluid according to an example of the present disclosure.
Figure 17:
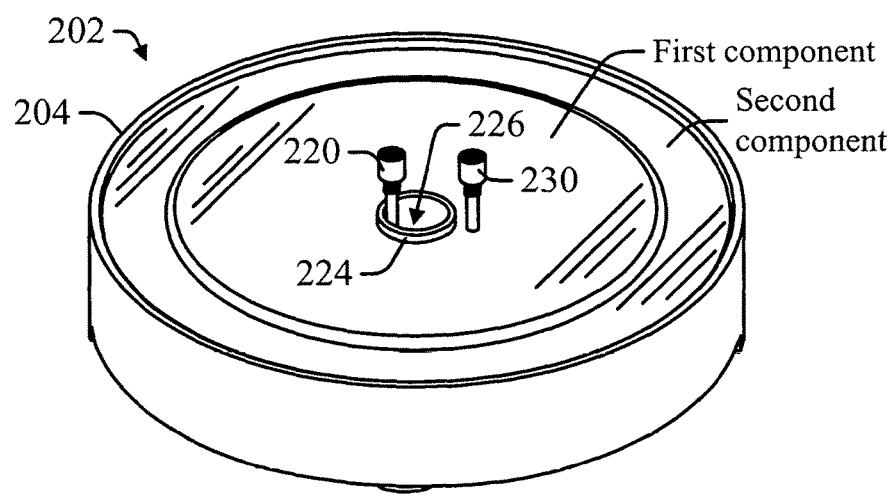
FIG. 17 is a perspective view of a drum rotor during centrifugation to fractionate a cell wash solution containing cellular fluid according to an example of the present disclosure.

As depicted in FIGS. 13-15, in an example, a drum rotor 200 for separating components of a multi-component fluid can include a separation rotor 202 including an outer wall 204 and an inner annular wall 206. The outer wall 204 can define a separation chamber 208 within the separation rotor 202 for receiving the multi-component fluid. As illustrated in FIG. 13, the inner annular wall 206 can be positioned to divide the separation chamber 108 into an inner annular space 210 and an outer annular space 212 arranged concentrically around the inner annular space 210. The drum rotor 200 can further include a bottom track 214 fluidly connected to the outer annular space 212 by a port 216. As illustrated in FIGS. 13 and 15, in examples, the drum rotor 200 can include a plurality of bottom tracks 214 that are each fluidly connected to the outer annular space 212 at different positions along the outer annular space 212. In this configuration, the plurality of bottom tracks 214 are fluidly connected with adjacent bottom tracks 214. In at least one example, the plurality of bottom tracks 214 are connected to a point proximate the center of the drum rotor 200.

As illustrated in FIGS. 13 and 14, in an example, the separation chamber 208 can further include a top cap 218 including a withdrawal port 220. The withdrawal port 220 can include a withdrawal tube 222 fluidly connecting the withdrawal port 220 to the bottom track 214. Fluid can be drawn from the outer annular space 212 through the bottom track 214 to the withdrawal tube 222. The bottom track 214 can be fluidly isolated from the inner annular space 210 such that fluid can be drawn from the outer annular space 210 without disturbing fluid retained in the inner annular space 210. In an example, the withdrawal tube 222 can be connected to a plurality of bottom tracks 214 proximate to the connection point of the plurality of bottom tracks 214 such that fluid can be simultaneously drawn from the outer annular space 212 at multiple points.

In an example, a multi-component fluid can be placed within the inner annular space 210. The multi-component fluid can comprise, but is not limited to, a wash solution in which wash fluids are added to cellular material to cleanse the cellular material. The drum rotor 200 can be rotated about a rotational axis α-α transecting the center of the separation rotor 202 such that denser materials or fluids (e.g. cellular material) are forced radially outward from the rotational axis α-α and over the inner annular wall 206 into the outer annular space 212. Light materials or fluids (e.g. wash fluids) remain proximate the rotational axis α-α and are generally retained within the inner annular space 210. In certain examples, a portion of the lighter materials or fluids can enter the outer annular space 212. Up to about 30-40% of the lighter materials can enter the outer annular space 212 with the heavier material. During rotation of the drum rotor 200, a brake can be applied to the drum rotor 200 to quickly stop the rotation of the drum rotor 200 to re-suspend separated solids captured in the outer annular space 212 within fluids in the outer annular space 212. The inner annular wall 206 can be sized to maintain separation of the fluids in the inner annular space 210 and the outer annular space 212 when the drum rotor 200 is not rotated. The stoppage of the drum rotor 200 also causes the separated materials to settle through the port 216 and enter the bottom track 214. In an example, the outer annular space 212 can have a slanted floor directing separated materials toward the port 216.

Figure 18:
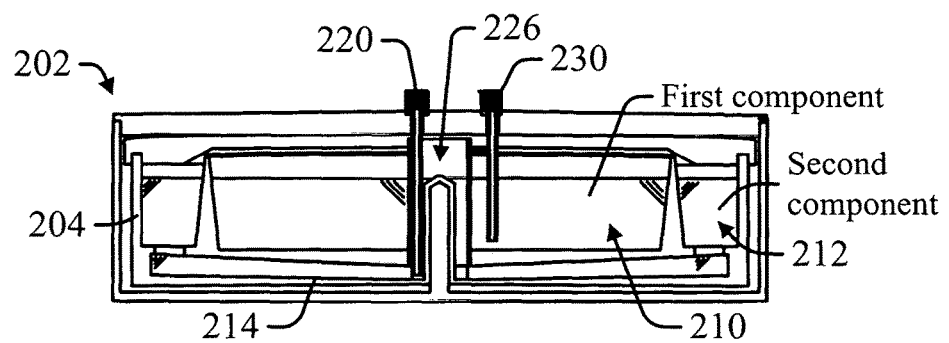
FIG. 18 is a cross-sectional side view of a drum rotor depicting settling of separated cellular material for withdrawal according to an example of the present disclosure.
Figure 19:
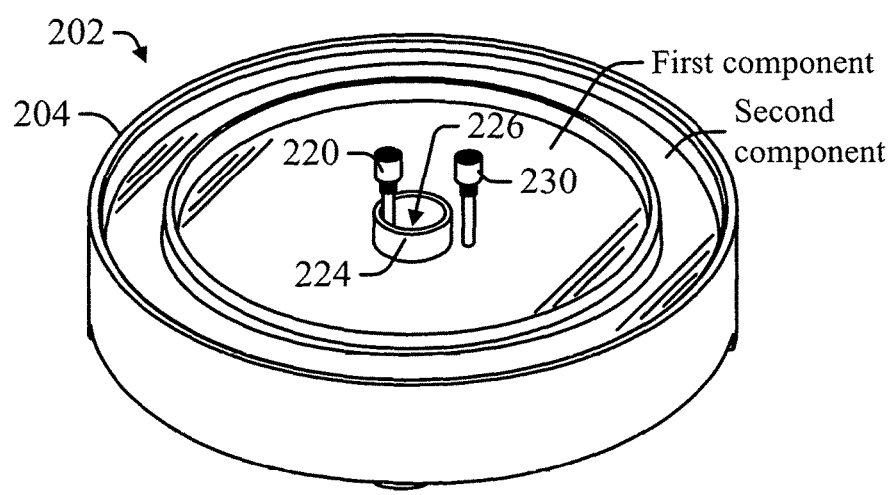
FIG. 19 is a perspective view of a drum rotor depicting settling of separated cellular material for withdrawal according to an example of the present disclosure.

As illustrated in FIGS. 18-19, in an example, a storage container (not shown) can be fluidly connected to the withdrawal port 220 to withdraw separated material collected within the bottom track 214. Withdrawing separated material within the bottom track 214 can draw additional separated material from the outer annular space 212 to until all the separated material within the separation rotor 202 is withdrawn. In an example, the bottom track 214 can be sloped toward the withdrawal tube 222 to facilitate drainage of the separated material from the outer annular space 212 and withdrawal of the separated material through the withdrawal tube 222. In an example, the top cap 218 can include an access hole 219, where the withdrawal port 220 extends through the access hole 219 permitting attachment of the storage container during rotation of the drum rotor 200.

As illustrated in FIGS. 18-19, in an example, the separation rotor 202 can further include an annular isolation wall 224 isolating a well space 226 from the inner annular space 212. The well space 226 can be connected to the bottom track 214 via a port 228 such that separated material initially collected within the outer annular space 212 travels through the bottom track 214 to collect within the well space 226. The withdrawal tube 212 can be positioned to collect the separated material within the well space 226 and draw the separated material from the separation rotor 202.

In an example, the top cap 218 can further include an inlet port 230 permitting the multicomponent fluid to be added to the separation chamber 208. The inlet port 230 can be positioned such that the administered fluid enters the inner annular space 212. In an example, the inlet port 230 can include an inlet tube 232 that can be positioned to draw fluid remaining in the inner annular space 212 through the inlet port 230 following the centrifugation of the separation rotor 202. The inlet port 230 extends through the access hole 219 permitting attachment of the multicomponent fluid source during rotation of the drum rotor 200.

In an example, the separation rotor 202 can include a rotor element 234 defining a port 236 for receiving a spindle 238 of a rotor cup 240 aligned with the rotational axis α-α such that the separation rotor 202 rotates about the rotational axis α-α. The separation rotor 202 can include at least one magnet holder 242 configured to receive a magnet 244. In this configuration, a magnetic field can be applied to the separation rotor 202 to rotate the separation rotor 202 about the rotational axis α-α. The rotor element 234 maintains the alignment of the separation rotor 202 with the rotational axis α-α as the separation rotor 202 is rotated by the magnets.

Figure 23:
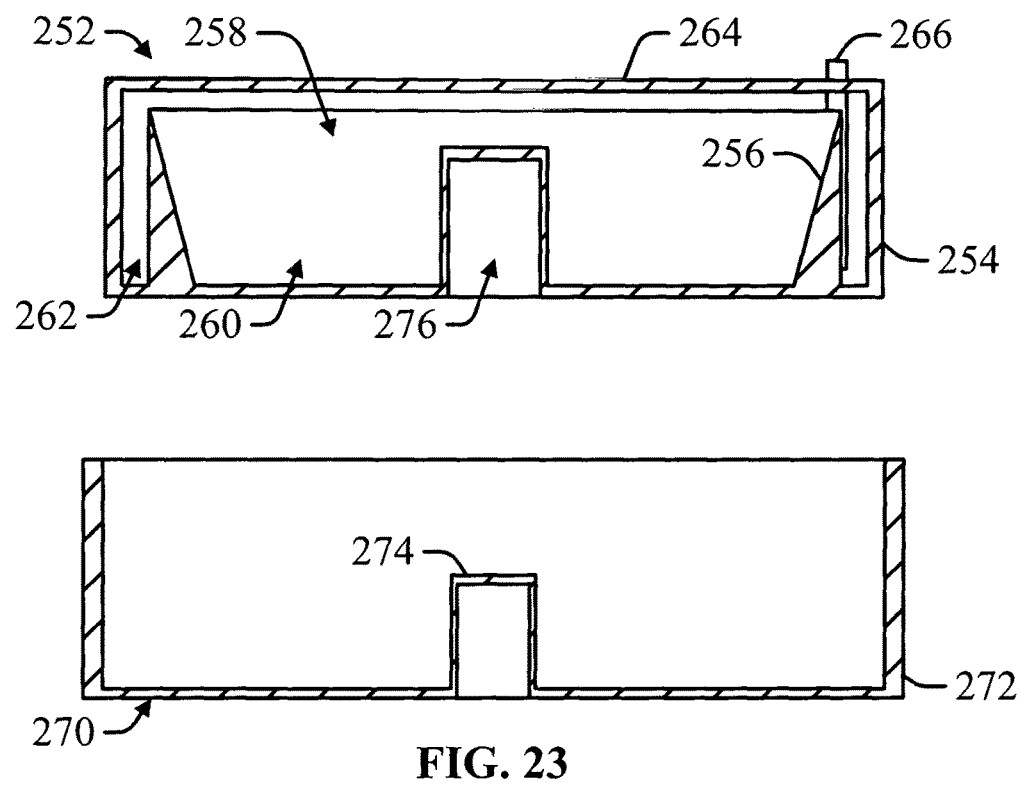
FIG. 23 is a side exploded, cross-sectional view of a drum rotor and a rotor cup according to an example of the present disclosure.

As depicted in FIGS. 20-23, in an example, a drum rotor 250 for separating components of a multi-component fluid can include a separation rotor 252 including an outer wall 254 and an annular inner wall 256. The outer wall 254 can define a separation chamber 258 within the separation rotor 202 for receiving the multi-component fluid. As illustrated in FIG. 23, the inner annular wall 256 can be positioned to divide the separation chamber 258 into an inner annular space 260 and an outer annular space 262 arranged concentrically around the inner annular space 260. The separation rotor 252 can include a top wall 264 enclosing the separation chamber 256. In an example, the outer wall 254, the annular inner wall 256, and the top wall 264 can be integral such that the separation chamber 258 is an integral unit.

In an example, the top wall 264 can include a withdrawal port 266 configured to receive a withdrawal member for withdrawing fluid from the separation chamber 256. The withdrawal port 266 can be positioned to align with the outer annular space 262 for withdrawing fluid within the outer annular space 262. A withdrawal member for a collection container can be inserted through the withdrawal port 266 into the outer annular space 262 to withdraw material collected within the outer annular space 262. The top wall 264 can also include an inlet port 268 configured to receive fluid into the separation chamber 256. The inlet port 268 can be positioned to align with the inner annular space 260 such that fluid entering the inlet port 268 enters the inner annular space 260.

In an example, a multi-component fluid can be placed within the inner annular space 260 with a collection medium. The multi-component fluid can comprise, but is not limited to, a wash solution in which a saline solution is added to red blood cells to cleanse the cellular material. In this configuration, the multi-component fluid containing the red blood cells suspended in the saline solution behaves like a solution with the overall density of the suspension. For example, a multi-component fluid having a 10% suspension of red blood cells in a saline has an overall density of 1.01. In this configuration, when the multi-component fluid is layered on a second solution have a greater density (e.g. 1.005), the red blood cells will sink through the suspending saline into the denser underlying collection medium. When the overall density of the red blood cell suspension is lower than that of an underlying medium, the suspended red blood cells will float on top of the higher density medium. Under the force of gravity or under centrifugation, the red blood cells will individually sediment through the underlying medium (provided its density is less than 1.1, that of a red blood cell), leaving the suspending medium (and dissolved contaminants) behind. A collection medium for drawing red blood cells from a saline suspending solution, can include, but are not limited to a 5% dextrose solution; a 9.25% sucrose solution; 10% LMD in a saline solution; <10% iron dextran solution; and a 10% dextran/5% dextrose solution.

The drum rotor 250 can be rotated about a rotational axis α-α transecting the center of the separation rotor 252 such that denser materials or fluids (e.g. red blood cells and the collection medium) are forced radially outward from the rotational axis α-α and over the inner annular wall 256 into the outer annular space 262. Light materials or fluids (e.g. the saline solution) remain proximate the rotational axis α-α and are generally retained within the inner annular space 260. During rotation of the drum rotor 250, a brake can be applied to the drum rotor 250 to quickly stop the rotation of the drum rotor 250 to re-suspend separated solids captured in the outer annular space 262 within the collection medium in the outer annular space 262. A withdrawal member for a collection container can be inserted through the withdrawal port 266 into the outer annular space 262 to withdraw the collection medium collected within the outer annular space 262.

As depicted in FIGS. 20-22, the separation rotor 252 can be received within a rotor cup 270. The rotor cup 270 can include a sidewall 272 defining a rotor space for receiving the separation rotor 252. In an example, the rotor cup 270 can include a spindle 274 aligned with the rotational axis α-α. In this configuration, the separation rotor 252 can include a rotor port 276 for receiving the spindle 274. The spindle 274 maintains alignment of the separation rotor 252 with the rotational axis α-α during rotation of the separation rotor 252.

Figure 24:
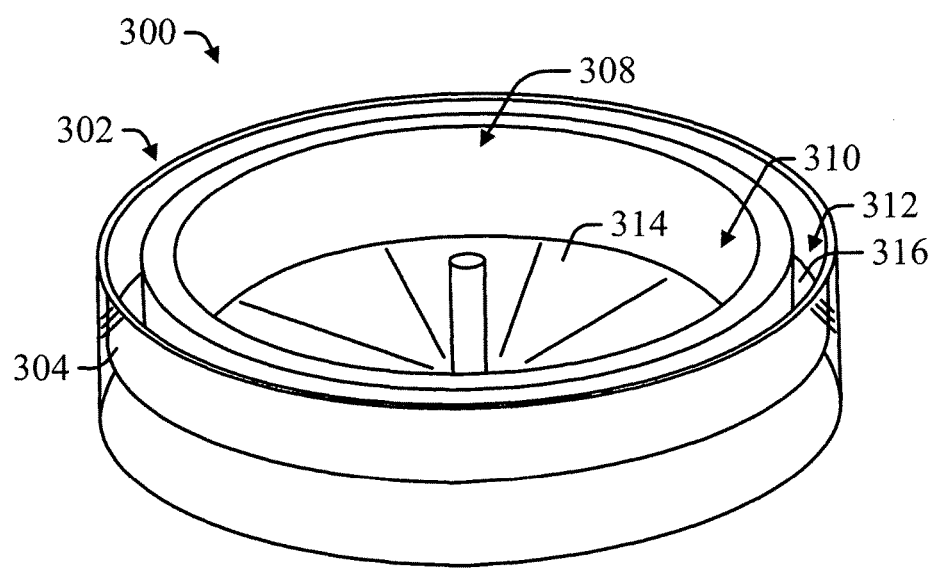
FIG. 24 is a perspective view of a drum rotor according to an example of the present disclosure.
Figure 25:
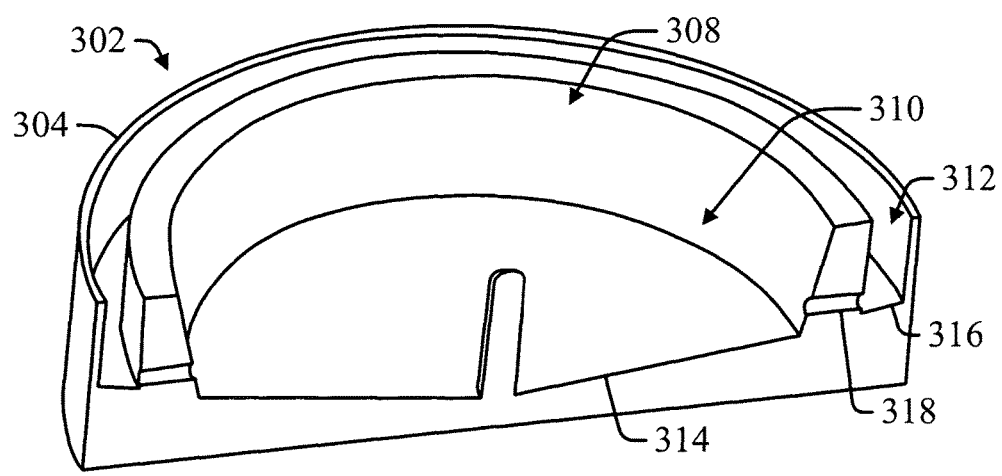
FIG. 25 is a cross-sectional perspective view of a separation rotor according to an example of the present disclosure.
Figure 26:
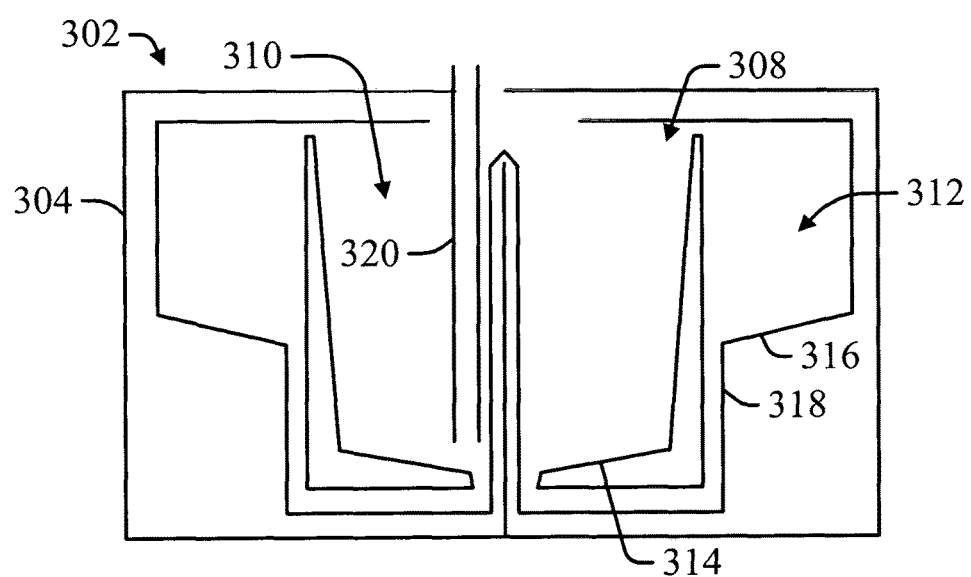
FIG. 26 is a perspective view of a separation rotor according to an example of the present disclosure.

As depicted in FIGS. 24-26, in an example, a drum rotor 300 for separating components of a multi-component fluid can include a separation rotor 302 including an outer wall 304 and an inner annular wall 306. The outer wall 304 can define a separation chamber 308 within the separation rotor 302 for receiving the multi-component fluid. As illustrated in FIG. 25, the inner annular wall 306 can be positioned to divide the separation chamber 308 into an inner annular space 310 and an outer annular space 312 arranged concentrically around the inner annular space 310. The inner annular space 310 can have an inner floor 314, and the outer annular space 312 can have an outer floor 316, wherein the outer floor 316 is positioned at a lower relative height to the inner floor 314. The inner annular wall 306 can include a drain port 318 permitting draining of fluid from the outer annular space 312 into the inner annular space 310. In an example, the drain port 318 can be positioned on the inner annular wall 306 proximate the outer floor 316.

In an example, a multi-component fluid can be placed within the inner annular space 310. The multi-component fluid can comprise, but is not limited to, a wash solution in which wash fluids are added to cellular material to cleanse the cellular material. The drum rotor 300 can be rotated about a rotational axis α-α transecting the center of the separation rotor 302 such that denser materials or fluids (e.g. cellular material) are forced radially outward from the rotational axis α-α and over the inner annular wall 306 into the outer annular space 312. Lighter materials or fluids (e.g. wash fluids) remain proximate the rotational axis α-α and are generally retained within the inner annular space 310. In certain examples, a portion of the lighter materials or fluids can enter the outer annular space 312. Following braking of the drum rotor 300, fluids and material collected in the outer annular space 312 can settle wherein liquid collected in the outer annular space 312 drains from the higher outer floor 316 through the drain port 318 into the inner annular space 310, which has a lower inner floor 314. In an example, the outer floor 316 can be angled toward the inner annular space 310 to facilitate draining of fluids within the outer annular space 312. In this configuration, solid materials, such as cellular material, are trapped within outer annular space 312 while fluid within the outer annular space 312 is drained. The solid materials can pack into the drain port 318 permitting fluids to be drained through the drain port 318 and restrict solid material from passing through the drain port 318.

As illustrated in FIG. 26, in an example, a withdrawal member 320 can be inserted into the inner annular space 310 of the separation rotor 302 to withdraw the supernatant collected in the inner annular space 310 following draining of the outer annular space 312.

As depicted in FIGS. 27-31, in an example, a drum rotor 350 for at least one component from a multi-component fluid can include a separation rotor 352 including an outer wall 354 defining a separation chamber 356. The separation rotor 352 can include a platform element 358 defining a platform surface 360 positioned a predetermined height H1 above the floor 362 of the separation rotor 352.

Figure 27:
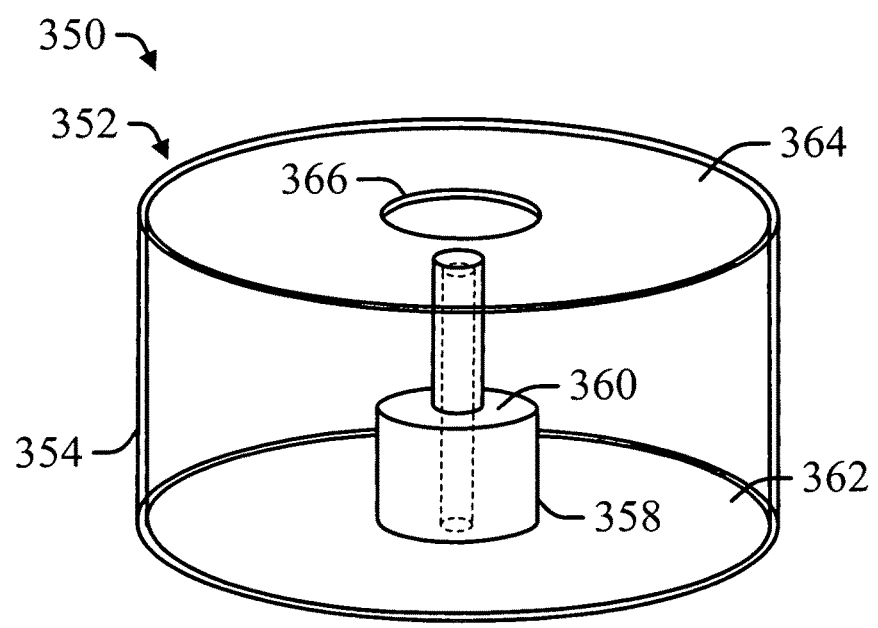
FIG. 27 is a perspective view of a separation rotor during centrifugation according to an example of the present disclosure.
Figure 28:
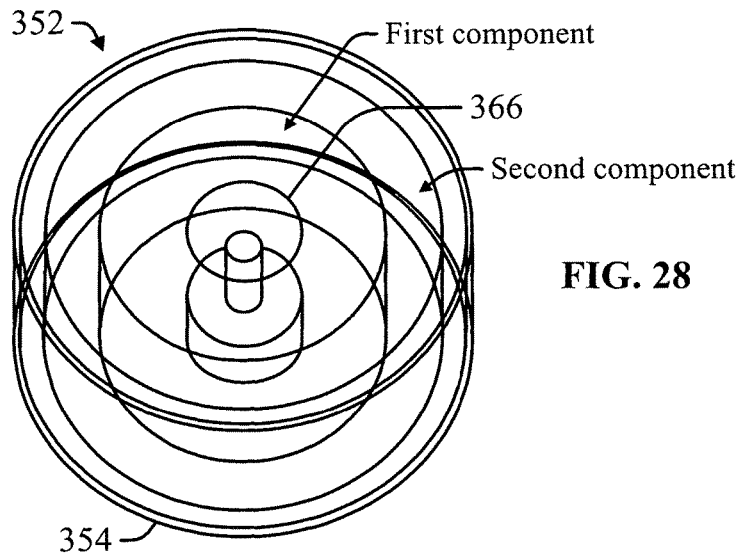
FIG. 28 is a perspective view of a separation rotor following centrifugation of the separation rotor and braking of the separation rotor according to an example of the present disclosure.
Figure 29:
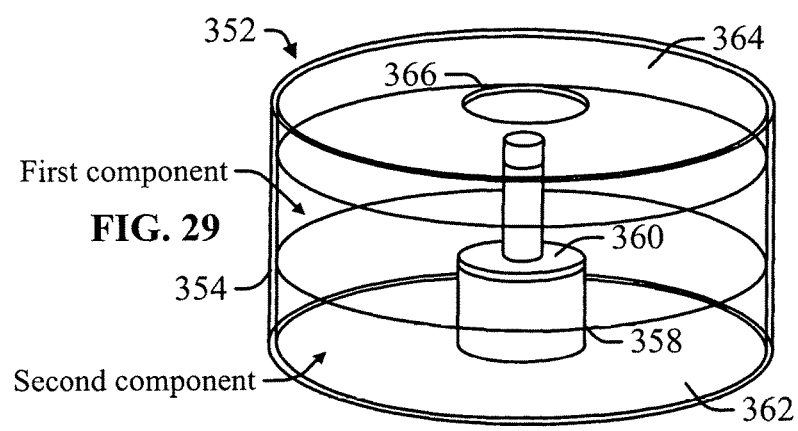
FIG. 29 is a schematic side view of a separation rotor according to an example of the present disclosure.
Figure 30:
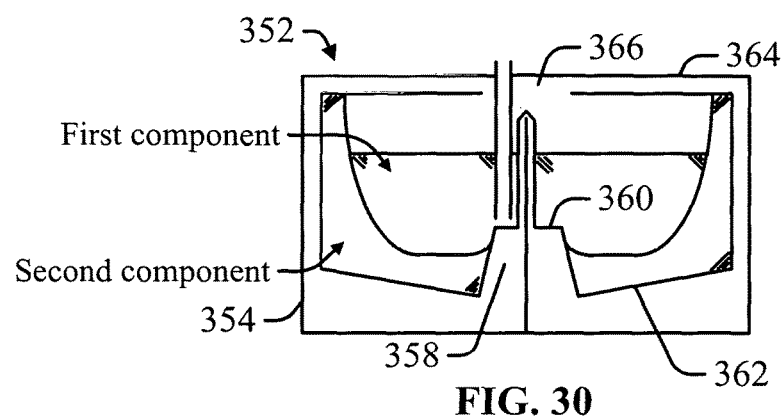
FIG. 30 is a schematic side view of a separation rotor following centrifugation and braking of the separation rotor according to an example of the present disclosure.
Figure 31:
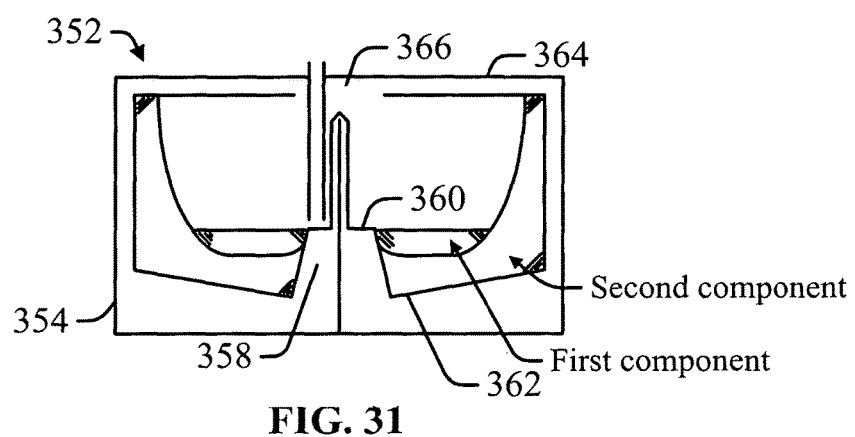
FIG. 31 is a schematic side view of a separation rotor following the withdrawal of wash fluid according to an example of the present disclosure.

In an example, a multi-component fluid can be received within the separation chamber 356. The separation rotor 362 can be rotated about a rotational axis α-α to fractionate the multi-component fluid into a plurality of components. The denser components can be positioned radially outward from the less dense components as illustrated in FIG. 27. Following braking of the separation rotor 362 to cease rotation of the separation rotor 362, the separated components can settle such that the denser components toward the floor 362 of the separation rotor 352, with the less dense components floating above the denser components. In an example, the predetermined height H1 of the platform surface 360 can correspond to a boundary between adjacent components. In this configuration, the platform surface 360 provides a guide for a withdrawal member to be inserted into the separation rotor 352 such that the component above the platform surface 360 can be drawn as illustrated in FIG. 30.

In an example, the separation rotor 352 can include a top wall 364 enclosing the separation chamber 356. The top wall 364 can include a withdrawal port 366 configured to receive a withdrawal member for withdrawing fluid from the separation chamber 356. The withdrawal port 366 can be positioned to align with the platform surface 360 such that inserting a withdrawal member into the separation chamber 356 through the withdrawal port 366 positions the withdrawal member adjacent the platform surface 360.

VARIOUS NOTES & EXAMPLES

Example 1 is a drum rotor for separating a multi-component fluid, comprising: a separation rotor including: an outer wall defining a separation chamber, an inner annular wall separating the separation chamber into an inner annular space and an outer annular space arranged concentrically around the inner annular space, and an outlet drain extending through the outer wall and in communication with the outer annular space for permitting drainage of fluid from the outer annular space; and a fluid bag fluidly connectable to the outlet drain for receiving fluid draining from the outer annular space; wherein the multi-component fluid is receivable within the inner annular space such that rotation of the separation rotor about a rotational axis forces at least one component from the multi-component fluid over the inner annular wall and into the outer annular space, wherein the rotational axis is centered within the inner annular wall such that the rotational axis intersects the inner annular space.

In Example 2, the subject matter of Example 1 optionally includes a top cap coupleable to the separation rotor to enclose the separation chamber.

In Example 3, the subject matter of Example 2 optionally includes wherein the top cap further comprises: an input opening in the top cap for delivering the multi-component fluid into the separation chamber; wherein the input opening is positioned on the top cap such that the multi-component fluid entering the separation chamber is received within the inner annular space.

In Example 4, the subject matter of any one or more of Examples 2-3 optionally include wherein the inner annular wall is shorter than the outer wall such that a gap is defined between the inner annular wall and the top cap when the top cap is coupled to the separation rotor.

In Example 5, the subject matter of any one or more of Examples 2-4 optionally include a bottom cap having a sidewall defining a bag chamber for receiving the fluid bag; wherein the bottom cap is coupleable to the top cap to permit the fluid bag to be connected to the outlet drain during rotation of the separation rotor.

In Example 6, the subject matter of any one or more of Examples 1-5 optionally include wherein the inner annular wall further comprises: an angled ramp face slanted toward the rotational axis for facilitating the transfer of the at least one component of the multi-component fluid into the outer annular space.

In Example 7, the subject matter of any one or more of Examples 1-6 optionally include wherein a floor of the outer annular space is slanted toward the output drain to funnel fluids toward the output drain.

In Example 8, the subject matter of any one or more of Examples 1-7 optionally include a bottom cap having a sidewall defining a bag chamber for receiving the fluid bag; wherein the bottom cap is coupleable to the separation rotor to permit the fluid bag to be connected to the outlet drain during rotation of the separation rotor.

In Example 9, the subject matter of any one or more of Examples 1-8 optionally include wherein the fluid bag is pre-sterilized.

In Example 10, the subject matter of Example 9 optionally includes wherein the separation rotor is a single use disposable component.

In Example 11, the subject matter of any one or more of Examples 1-10 optionally include wherein the fluid bag further comprises: a tube connector fluidly connectable to the fluid bag to the output drain; wherein the tube connector is pre-sterilized.

Example 12 is a separation system for separating a multi-component fluid, comprising: a centrifuge device having a rotor cup rotatable about a rotational axis; a separation rotor including: an outer wall defining a separation chamber, an inner annular wall separating the separation chamber into an inner annular space and an outer annular space arranged concentrically around the inner annular space, and an outlet drain through the outer wall at the outer annular space permitting drainage of fluid from the outer annular space, wherein the separation rotor is receivable within the rotor cup; and a fluid bag fluidly connectable to the outlet drain for receiving fluid draining from the outer annular space; wherein the multi-component fluid is receivable within the inner annular space such that rotation of the rotor cup rotates the separation rotor about a rotational axis forces at least one component from the multi-component fluid over the inner annular wall and into the outer annular space, wherein the rotational axis is centered within the inner annular wall such that the rotational axis intersects the inner annular space.

In Example 13, the subject matter of Example 12 optionally includes a top cap coupleable to the separation rotor to enclose the separation chamber.

In Example 14, the subject matter of Example 13 optionally includes wherein the top cap further comprises: an input opening in the top cap for delivering the multi-component fluid into the separation chamber; wherein the input opening is positioned on the top cap such that the multi-component fluid entering the separation chamber is received within the inner annular space.

In Example 15, the subject matter of any one or more of Examples 13-14 optionally include wherein the inner annular wall is shorter than the outer wall such that a gap is defined between the inner annular wall and the top cap when the top cap is coupled to the separation rotor.

In Example 16, the subject matter of any one or more of Examples 13-15 optionally include a bottom cap having a sidewall defining a bag chamber for receiving the fluid bag; wherein the bottom cap is coupleable to the top cap to permit the fluid bag to be connected to the outlet drain during rotation of the separation rotor.

In Example 17, the subject matter of any one or more of Examples 12-16 optionally include wherein the inner annular wall further comprises: an angled ramp face slanted toward the rotational axis for facilitating the transfer of the at least one component of the multi-component fluid into the outer annular space.

In Example 18, the subject matter of any one or more of Examples 12-17 optionally include wherein a floor of the outer annular space is slanted toward the output drain to funnel fluids toward the output drain.

In Example 19, the subject matter of any one or more of Examples 12-18 optionally include a bottom cap having a sidewall defining a bag chamber for receiving the fluid bag; wherein the bottom cap is coupleable to the separation rotor to permit the fluid bag to be connected to the outlet drain during rotation of the separation rotor.

In Example 20, the subject matter of any one or more of Examples 12-19 optionally include wherein the fluid bag is pre-sterilized.

In Example 21, the subject matter of Example 20 optionally includes wherein the separation rotor is a single use disposable element.

In Example 22, the subject matter of any one or more of Examples 12-21 optionally include wherein the fluid bag further comprises: a tube connector fluidly connectable to the fluid bag to the output drain; wherein the tube connector is pre-sterilized.

Example 23 is a drum rotor for separating a multi-component fluid, comprising: a separation rotor including: an outer wall defining a separation chamber, and an inner annular wall separating the separation chamber into an inner annular space and an outer annular space arranged concentrically around the inner annular space; and a top cap including a withdrawal port positioned to align with the outer annular space; wherein the multi-component fluid is receivable within the inner annular space such that rotation of the separation rotor about a rotational axis to force at least one component from the multi-component fluid over the inner annular wall and into the outer annular space, wherein the rotational axis is centered within the inner annular wall such that the rotational axis intersects the inner annular space; wherein a withdrawal member is insertable through the withdrawal port to draw material received within the outer annular space.

In Example 24, the subject matter of Example 23 optionally includes wherein the top cap further comprises: an input opening in the top cap for delivering the multi-component fluid into the separation chamber; wherein the input opening is positioned on the top cap such that the multi-component fluid entering the separation chamber is received within the inner annular space.

In Example 25, the subject matter of any one or more of Examples 23-24 optionally include a rotor cup including a sidewall defining a rotor space for receiving the separation rotor.

In Example 26, the subject matter of Example 25 optionally includes the rotor cup further comprising: at least one engagement feature for engaging the separation rotor to a centrifuge system for rotating the rotor cup and correspondingly the separation rotor received within the rotor space.

In Example 27, the subject matter of any one or more of Examples 23-26 optionally include wherein the inner annular wall further comprises: an angled ramp face slanted toward the rotational axis for facilitating the transfer of the at least one component of the multi-component fluid into the outer annular space.

Example 28 is a separation system for separating a multi-component fluid, comprising: a rotor cup including a sidewall defining a rotor space; a separation rotor including: an outer wall defining a separation chamber, and an inner annular wall separating the separation chamber into an inner annular space and an outer annular space arranged concentrically around the inner annular space, wherein the separation rotor is receivable within the rotor space of the rotor cup; and a top cap including a withdrawal port positioned to align with the outer annular space; wherein the multi-component fluid is receivable within the inner annular space such that rotation of the separation rotor about a rotational axis forces at least one component from the multi-component fluid over the inner annular wall and into the outer annular space, wherein the rotational axis is centered within the inner annular wall such that the rotational axis intersects the inner annular space; wherein a withdrawal member is insertable through the withdrawal port to draw material received within the outer annular space.

In Example 29, the subject matter of Example 28 optionally includes wherein the top cap further comprises: an input opening in the top cap for delivering the multi-component fluid into the separation chamber; wherein the input opening is positioned on the top cap such that the multi-component fluid entering the separation chamber is received within the inner annular space.

In Example 30, the subject matter of any one or more of Examples 28-29 optionally include the rotor cup further comprising: at least one engagement feature for engaging the separation rotor to a centrifuge system for rotating the rotor cup and correspondingly the separation rotor received within the rotor space.

In Example 31, the subject matter of any one or more of Examples 28-30 optionally include wherein the inner annular wall further comprises: an angled ramp face slanted toward the rotational axis for facilitating the transfer of the at least one component of the multi-component fluid into the outer annular space.

Example 32 is a drum rotor for separating a multi-component fluid, comprising: a separation rotor including: an outer wall defining a separation chamber, an inner annular wall separating the separation chamber into an inner annular space and an outer annular space arranged concentrically around the inner annular space, and a bottom track fluidly connected to the outer annular space by a port; and a top cap including a withdrawal port fluidly connected to the bottom track by a withdrawal tube; wherein the multi-component fluid is receivable within the inner annular space such that rotation of the separation rotor about a rotational axis forces at least one component from the multi-component fluid over the inner annular wall and into the outer annular space, wherein the rotational axis is centered within the inner annular wall such that the rotational axis intersects the inner annular space; wherein the at least one component is drained through the port into the bottom track and withdrawn from the separation rotor through the withdrawal tube and withdrawal port.

In Example 33, the subject matter of Example 32 optionally includes wherein the bottom track is slanted toward the withdrawal tube to direct the at least one component toward the withdrawal tube for withdrawal from the separation rotor.

In Example 34, the subject matter of any one or more of Examples 32-33 optionally include wherein the top cap further includes an access port through which the withdrawal port is positioned; wherein a collection container is fluidly connected to the withdrawal port during rotation for continuous withdrawal of separated components of the multi-fluid component.

In Example 35, the subject matter of Example 34 optionally includes an input port in the top cap for delivering the multi-component fluid into the separation chamber; wherein the input opening is positioned on the top cap such that the multi-component fluid entering the separation chamber is received within the inner annular space.

In Example 36, the subject matter of Example 35 optionally includes wherein the input port extends through the access port; wherein the input port is connected to a fluid supply for continuously receiving multi-component fluid into the separation rotor during separation.

In Example 37, the subject matter of Example 36 optionally includes wherein the input port further includes: an input tube insertable into the inner annular space for supplying the multi-component fluid into the inner annular space and withdrawing at least one component of the multi-component fluid retained within the inner annular space following separation.

In Example 38, the subject matter of any one or more of Examples 32-37 optionally include wherein the outer wall defines at least one magnet holder for receiving a magnet; wherein a magnetic field can be applied to the separation rotor to induce rotation of the separation rotor about the rotational axis.

In Example 39, the subject matter of Example 38 optionally includes wherein the separation rotor further comprises: a bearing element defining a port; wherein the port is sized to receive a guide spindle aligned with the rotational axis of the separation rotor to guide rotation of the separation rotor about the rotational axis.

In Example 40, the subject matter of any one or more of Examples 32-39 optionally include an annular isolation wall isolating a well space within the inner annular space; wherein the well space is fluidly connected to the bottom track by a port.

In Example 41, the subject matter of Example 40 optionally includes wherein the withdrawal tube is positioned within the well space to draw the at least one component collected within the well space.

Example 42 is a drum rotor for separating a multi-component fluid, comprising: a separation rotor including: an outer wall defining a separation chamber, an inner annular wall separating the separation chamber into an inner annular space and an outer annular space arranged concentrically around the inner annular space, and a top wall including a withdrawal port positioned to align with the outer annular space; wherein the multi-component fluid is receivable within the inner annular space such that rotation of the separation rotor about a rotational axis forces at least one component from the multi-component fluid over the inner annular wall and into the outer annular space, wherein the rotational axis is centered within the inner annular wall such that the rotational axis intersects the inner annular space; wherein a withdrawal member is insertable through the withdrawal port to draw material received within the outer annular space.

In Example 43, the subject matter of Example 42 optionally includes wherein the separation rotor is receivable within a rotor space defined by a rotor cup.

In Example 44, the subject matter of Example 43 optionally includes wherein the separation rotor further comprises: a bearing element defining a port; wherein the port is sized to receive a guide spindle of the rotor cup aligned with the rotational axis of the separation rotor to guide rotation of the separation rotor about the rotational axis.

Example 45 is a separation system for separating a multi-component fluid, comprising: a rotor cup defining a rotor space; and a separation rotor including: an outer wall defining a separation chamber, an inner annular wall separating the separation chamber into an inner annular space and an outer annular space arranged concentrically around the inner annular space, and a top wall including a withdrawal port positioned to align with the outer annular space; wherein the separation rotor is receivable within the rotor cup; wherein the multi-component fluid is receivable within the inner annular space such that rotation of rotor cup rotates the separation rotor forcing at least one component from the multi-component fluid over the inner annular wall and into the outer annular space, wherein the rotational axis is centered within the inner annular wall such that the rotational axis intersects the inner annular space; wherein a withdrawal member is insertable through the withdrawal port to draw material received within the outer annular space.

Example 46 is a drum rotor for separating a multi-component fluid, comprising: a separation rotor including: an outer wall defining a separation chamber, and an inner annular wall separating the separation chamber into an inner annular space and an outer annular space arranged concentrically around the inner annular space, wherein the inner annular space having an inner floor having a lower height than an outer floor of the outer annular space wherein the multi-component fluid is receivable within the inner annular space such that rotation of the separation rotor about a rotational axis forces at least one component from the multi-component fluid over the inner annular wall and into the outer annular space, wherein the rotational axis is centered within the inner annular wall such that the rotational axis intersects the inner annular space.

In Example 47, the subject matter of Example 46 optionally includes wherein the inner annular wall defines at least one drain port permitting drainage of fluid from the outer annular space into the inner annular space.

In Example 48, the subject matter of Example 47 optionally includes wherein the at least one drain port is positioned proximate to the outer floor and bottom of the outer annular space.

In Example 49, the subject matter of any one or more of Examples 47-48 optionally include wherein the outer floor is sloped toward the rotational axis to facilitate draining of fluid through the at least one drain port.

In Example 50, the subject matter of any one or more of Examples 47-49 optionally include wherein the drain port is fluidly connectable to a drain channel to direct fluid to a drain outlet in the inner annular space proximate the rotational axis.

In Example 51, the subject matter of any one or more of Examples 46-50 optionally include wherein the inner floor is sloped downward toward the rotational axis.

In Example 52, the subject matter of any one or more of Examples 46-51 optionally include a top wall including a withdrawal port positioned to align with the inner annular space; wherein a withdrawal member is insertable through the withdrawal port to draw material retained within the inner annular space.

In Example 53, the subject matter of any one or more of Examples 46-52 optionally include wherein the separation rotor is receivable within a rotor space defined by a rotor cup.

In Example 54, the subject matter of Example 53 optionally includes wherein the separation rotor further comprises: a bearing element defining a port; wherein the port is sized to receive a guide spindle of the rotor cup aligned with the rotational axis of the separation rotor to guide rotation of the separation rotor about the rotational axis.

Example 55 is a drum rotor for separating a multi-component fluid, comprising: a separation rotor including: an outer wall defining a separation chamber and a floor, and a platform element defining a platform surface positioned at a predetermined height above the floor, wherein the multi-component fluid and a separation medium are received within the inner annular space such that rotation of the separation rotor draws solid components within the multi-component fluid are drawn into the separation medium; wherein the separation medium is has a higher density than the multi-component fluid.

In Example 56, the subject matter of Example 55 optionally includes wherein the predetermined height corresponds to the volume of the separation medium added to the separation rotor such that the transition boundary between the multi-component fluid and the separation medium approximates the predetermined height of the platform surface.

In Example 57, the subject matter of Example 56 optionally includes a top wall defining an access port; wherein a collection container is insertable into the access port until proximate to the platform surface for drawing the multi-component fluid from the separation rotor.

Example 58 is a drum rotor for separating a multi-component fluid, comprising: a separation rotor including: an outer wall defining a separation chamber and a floor, and a platform element defining a platform surface positioned at a predetermined height above the floor, wherein the multi-component fluid and a separation medium are received within the inner annular space such that rotation of the separation rotor draws solid components from fluids of the multi-component fluid.

In Example 59, the subject matter of any one or more of Examples 55-58 optionally include wherein the predetermined height corresponds to the volume of solids separated from the multi-component fluid is less than the predetermined height of the platform element.

In Example 60, the subject matter of Example 59 optionally includes a top wall defining an access port; wherein a collection container is insertable into the access port until proximate to the platform surface for drawing the fluids of the multi-component fluid from the separation rotor. Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the present subject matter can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the present subject matter should be determined with reference to the appended claims, along with the full scope of equivalents to which such claims are entitled.

What is claimed is:

1. A drum rotor for separating a multi-component fluid, comprising:
   a separation rotor including:
      an outer wall defining a separation chamber,
      an inner annular wall separating the separation chamber into an inner annular space and an outer annular space arranged concentrically around the inner annular space, and
      an outlet drain extending through the outer wall and in communication with the outer annular space for permitting drainage of fluid from the outer annular space; and
   a fluid bag fluidly connectable to the outlet drain for receiving fluid draining from the outer annular space;
   wherein the multi-component fluid is receivable within the inner annular space such that rotation of the separation rotor about a rotational axis forces at least one component from the multi-component fluid over the inner annular wall and into the outer annular space, wherein the rotational axis is centered within the inner annular wall such that the rotational axis intersects the inner annular space.

2. The drum rotor of claim 1, further comprising:
   a top cap coupleable to the separation rotor to enclose the separation chamber.

3. The drum rotor of claim 2, wherein the top cap further comprises:
   an input opening in the top cap for delivering the multi-component fluid into the separation chamber;
   wherein the input opening is positioned on the top cap such that the multi-component fluid entering the separation chamber is received within the inner annular space.

4. The drum rotor of claim 2, wherein the inner annular wall is shorter than the outer wall such that a gap is defined between the inner annular wall and the top cap when the top cap is coupled to the separation rotor.

5. The drum rotor of claim 2, further comprising:
   a bottom cap having a sidewall defining a bag chamber for receiving the fluid bag;
   wherein the bottom cap is coupleable to the top cap to permit the fluid bag to be connected to the outlet drain during rotation of the separation rotor.

6. The drum rotor of claim 1, wherein the inner annular wall further comprises:
   an angled ramp face slanted toward the rotational axis for facilitating the transfer of the at least one component of the multi-component fluid into the outer annular space.

7. The drum rotor of claim 1, wherein a floor of the outer annular space is slanted toward the output drain to funnel fluids toward the output drain.

8. The drum rotor of claim 1, further comprising:
   a bottom cap having a sidewall defining a bag chamber for receiving the fluid bag;
   wherein the bottom cap is coupleable to the separation rotor to permit the fluid bag to be connected to the outlet drain during rotation of the separation rotor.

9. The drum rotor of claim 1, wherein the fluid bag is pre-sterilized;
   wherein the separation rotor is a single use disposable component.

10. The drum rotor of claim 1, wherein the fluid bag further comprises:
    a tube connector fluidly connectable to the fluid bag to the output drain;
    wherein the tube connector is pre-sterilized.

11. A separation system for separating a multi-component fluid, comprising:
    a centrifuge device having a rotor cup rotatable about a rotational axis;
    a separation rotor including:
       an outer wall defining a separation chamber,
       an inner annular wall separating the separation chamber into an inner annular space and an outer annular space arranged concentrically around the inner annular space, and
       an outlet drain through the outer wall at the outer annular space permitting drainage of fluid from the outer annular space,
       wherein the separation rotor is receivable within the rotor cup; and
    a fluid bag fluidly connectable to the outlet drain for receiving fluid draining from the outer annular space;
    wherein the multi-component fluid is receivable within the inner annular space such that rotation of the rotor cup rotates the separation rotor about a rotational axis forces at least one component from the multi-component fluid over the inner annular wall and into the outer annular space, wherein the rotational axis is centered within the inner annular wall such that the rotational axis intersects the inner annular space.

12. The separation system of claim 11, further comprising:
    a top cap coupleable to the separation rotor to enclose the separation chamber.

13. The separation system of claim 12, wherein the top cap further comprises:
    an input opening in the top cap for delivering the multi-component fluid into the separation chamber;
    wherein the input opening is positioned on the top cap such that the multi-component fluid entering the separation chamber is received within the inner annular space.

14. The separation system of claim 12, wherein the inner annular wall is shorter than the outer wall such that a gap is defined between the inner annular wall and the top cap when the top cap is coupled to the separation rotor.

15. The separation system of claim 12, further comprising:
    a bottom cap having a sidewall defining a bag chamber for receiving the fluid bag;
    wherein the bottom cap is coupleable to the top cap to permit the fluid bag to be connected to the outlet drain during rotation of the separation rotor.

16. The separation system of claim 11, wherein the inner annular wall further comprises:
    an angled ramp face slanted toward the rotational axis for facilitating the transfer of the at least one component of the multi-component fluid into the outer annular space.

17. The separation system of claim 11, wherein a floor of the outer annular space is slanted toward the output drain to funnel fluids toward the output drain.

18. The separation system of claim 11, further comprising:

a bottom cap having a sidewall defining a bag chamber for receiving the fluid bag;
wherein the bottom cap is coupleable to the separation rotor to permit the fluid bag to be connected to the outlet drain during rotation of the separation rotor.

19. The separation system of claim 11, wherein the fluid bag is pre-sterilized; and
wherein the separation rotor is a single use disposable element.

20. The separation system of claim 11, wherein the fluid bag further comprises:
a tube connector fluidly connectable to the fluid bag to the output drain;
wherein the tube connector is pre-sterilized.

* * * * *